United States Patent
Yoshioka et al.

(10) Patent No.: US 6,699,382 B2
(45) Date of Patent: Mar. 2, 2004

(54) METHOD FOR ANALYZING A BIOLOGICAL SAMPLE

(75) Inventors: Toshihiko Yoshioka, Hirakata (JP); Shin Ikeda, Katano (JP); Motokazu Watanabe, Kadoma (JP); Shiro Nankai, Hirakata (JP)

(73) Assignee: Matsushita Electric Industrial Co., Ltd., Osaka-fu (JP)

( * ) Notice: Subject to any disclaimer, the term of this patent is extended or adjusted under 35 U.S.C. 154(b) by 0 days.

(21) Appl. No.: 10/235,451

(22) Filed: Sep. 4, 2002

(65) Prior Publication Data

US 2003/0000834 A1 Jan. 2, 2003

Related U.S. Application Data

(62) Division of application No. 09/327,017, filed on Jun. 7, 1999, now abandoned.

(30) Foreign Application Priority Data

Jun. 11, 1998 (JP) ............................................. 10-163375

(51) Int. Cl.[7] ............................................. G01N 27/327
(52) U.S. Cl. ............................. 205/777.5; 204/403.01; 204/403.09; 204/403.1; 204/403.11; 204/403.14
(58) Field of Search ........................... 204/403.01, 435, 204/418, 416, 403.04, 403.09, 403.1, 403.11, 403.14; 205/777.5, 778

(56) References Cited

U.S. PATENT DOCUMENTS

| | | |
|---|---|---|
| 3,151,052 A | 9/1964 | Arthur et al. |
| 3,424,664 A | 1/1969 | Severing Haus |
| 3,556,950 A | 1/1971 | Dahms |
| 4,533,457 A | 8/1985 | Watanabe |
| 4,844,787 A | 7/1989 | Akao et al. |
| 4,966,671 A | 10/1990 | Nylander et al. |
| 5,130,009 A | 7/1992 | Marsoner et al. |
| 5,141,868 A | 8/1992 | Shanks et al. |
| 5,228,972 A * | 7/1993 | Osaka et al. |
| 5,385,846 A | 1/1995 | Kuhn et al. |
| 5,395,503 A | 3/1995 | Parce et al. |
| 5,437,999 A | 8/1995 | Diebold et al. |
| 5,705,045 A | 1/1998 | Park et al. |
| 5,723,345 A | 3/1998 | Yamauchi et al. |

FOREIGN PATENT DOCUMENTS

| | | |
|---|---|---|
| DE | 195 46 535 A1 | 6/1997 |
| EP | 0 226 470 A2 | 6/1987 |
| EP | 0 351 891 A2 | 1/1990 |
| EP | 0 590 661 A1 | 4/1994 |
| EP | 0 730 037 A2 | 9/1996 |
| EP | 0 795 601 A2 | 9/1997 |
| EP | 0 811 838 A1 | 12/1997 |
| EP | 0 872 728 A1 | 10/1998 |
| GB | 2 254 436 A | 10/1992 |
| JP | 60244853 | 12/1985 |
| JP | 61002060 | 1/1986 |
| JP | 03202764 A | 9/1991 |
| JP | 04-194660 A | 7/1992 |
| JP | 09-084781 A | 3/1997 |
| WO | WO 95/10223 A2 | 4/1995 |

* cited by examiner

Primary Examiner—T. Tung
(74) Attorney, Agent, or Firm—Akin Gump Strauss Hauer & Feld LLP

(57) ABSTRACT

A biosensor enabling accurate measurement of the concentration of a substrate contained in a trace amount of a sample solution is disclosed. The electrochemical analysis element in accordance with the present invention which should be included in the biosensor comprises a sensor body having a hollow space which space is open at its both ends, an electrode system having a working electrode and a counter electrode, a reagent segment containing an enzyme, wherein the electrode system and the reagent segment are disposed on an inner wall of the hollow space.

18 Claims, 6 Drawing Sheets

METHOD FOR ANALYZING A BIOLOGICAL SAMPLE

CROSS-REFERENCE TO RELATED APPLICATION

This is a division of U.S. patent application Ser. No. 09/327,017, filed Jun. 7, 1999 for "Electrochemical Analysis Element," now abandoned.

BACKGROUND OF THE INVENTION

The present invention relates to an electrochemical analysis element that facilitates rapid and accurate quantitation of a specific component contained in a biological sample such as blood, sweat or the like, or food sample such as food raw material or food product from food industries.

The biosensor disclosed in the Japanese Laid-Open Patent Publication No Hei 3-202764 is a known example of electrochemical analysis element that facilitates simplified quantitation of a specific component, that is, a substrate contained in a biological or food sample without necessitating dilution and subsequent stirring of a sample solution. The biosensor disclosed in this reference is produced by first forming an electrode system on an insulating base plate using screen printing method or the like and subsequently forming a reaction layer containing an oxidoreductase and an electron acceptor on the formed electrode system.

This biosensor quantitates the substrate concentration in a sample by the following procedure.

First, dropping a sample solution on the reaction layer of the biosensor dissolves the reaction layer in the sample solution, which promotes enzyme reaction between the substrate in the sample solution and the oxidoreductase in the reaction layer. Upon enzyme reaction, the electron acceptor in the reaction layer is reduced. A voltage is applied across the electrodes of the sensor after a predetermined time to electrochemically oxidize the reduced electron acceptor. The substrate concentration in the sample is quantitated based on the oxidation current value across the electrodes.

The prior art electrochemical analysis element can readily determine the substrate concentration in a sample of several $\mu$l or more. However, such element has a drawback that it sometimes meets difficulties in making reliable measurement if the sample is very small in amount under several $\mu$l.

BRIEF SUMMARY OF THE INVENTION

The object of the present invention is therefore to provide an electrochemical analysis element that enables reliable measurement of a trace amount of sample.

The electrochemical analysis element in accordance with the present invention comprises a sensor body having a hollow space which space is open at its both ends, an electrode system having a working electrode and a counter electrode and a reagent segment containing an enzyme, wherein the electrode system and the reagent segment are disposed on an inner wall of the hollow space.

In a preferred mode of the present invention, the working electrode is positioned to oppose to the counter electrode on the inner wall of the hollow space.

In another preferred mode of the present invention, the reagent segment further comprises an electron acceptor.

In still another preferred mode of the present invention, the reagent segment is disposed on the working electrode.

When the sample is whole blood, an arrangement of a filter on at least one open end of the hollow space helps to filter red blood cells during passage of the whole blood through the filter. This eliminates inconveniences due to arrival and interference of red blood cells at the reagent segment.

Closure of both open ends of the hollow space with a resin film or aluminum laminate film can enhance reliable preservation of the reagents in the reagent segment.

According to the present invention, a provision of a reagent segment containing glucose oxidase yields an electrochemical analysis element that can quantitate glucose in body fluids. A provision of a reagent segment containing cholesterol oxidase in combination with cholesterol esterase yields another electrochemical analysis element that can quantitate cholesterol in body fluids.

While the novel features of the invention are set forth particularly in the appended claims, the invention, both as to organization and content, will be better understood and appreciated, along with other objects and features thereof, from the following detailed description taken in conjunction with the drawings.

DETAILED DESCRIPTION OF THE INVENTION

In the following, the present invention will be described more specifically referring to preferred examples of the electrochemical analysis element. In the figures, common numeral numbers have been used for identical parts.

Figure 1:
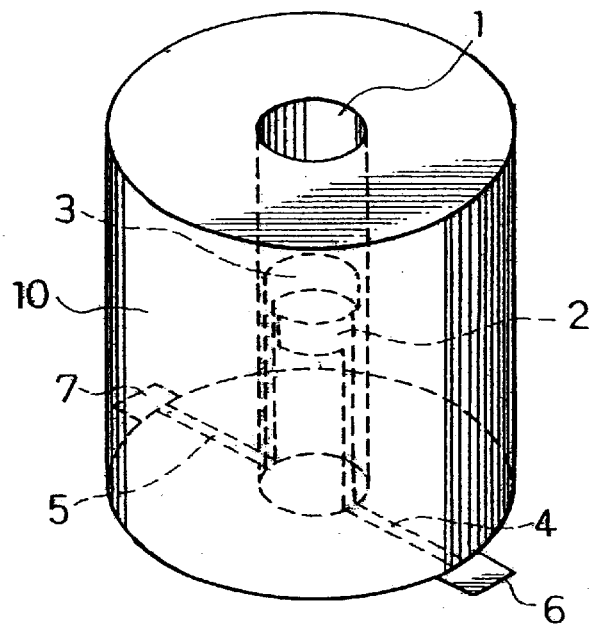
FIG. 1 is an oblique view illustrating an electrochemical analysis element in accordance with one example of the present invention from which the reagent segment has been omitted.
Figure 2:
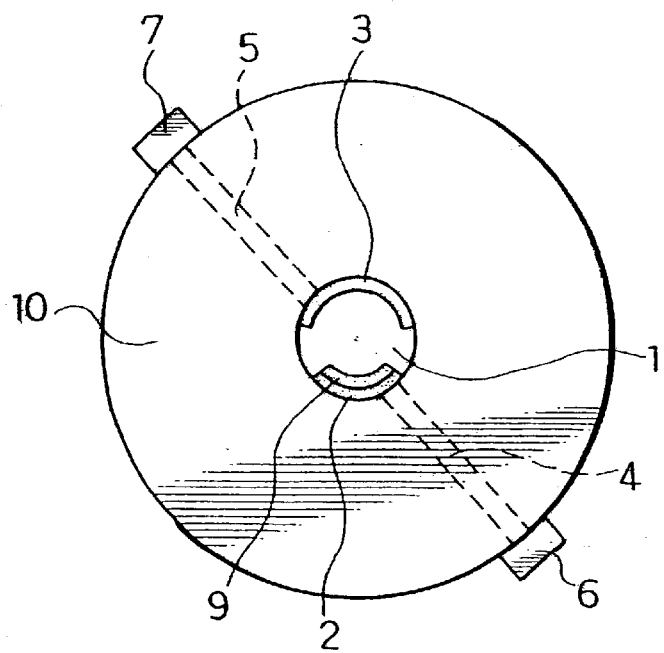
FIG. 2 is a plan view of the same element.

FIG. 1 is an external view of a representative electrochemical analysis element in accordance with the present invention and FIG. 2 is a plan view of the element of FIG. 1.

A cylindrical sensor body 10 made of an electrically insulating material has a cylindrical hollow space 1 in the center. On the inner wall of the hollow space, an electrode system having a working electrode 2 and a counter electrode 3 is disposed and leads 4, 5 which are connected to the respective electrodes are also formed. A reagent segment 9 containing an enzyme is formed on the working electrode 2. The leads 4, 5 which are connected to the working electrode 2 and the counter electrode 3, respectively, are protruding at the lead tip outside from the bottom of the sensor body to function as a lead connector 6 or a lead connector 7. In FIG. 1, the reagent segment 9 and an insulating layer for coating the lead 4 of the working electrode 2 have been omitted. Coating of the lead 4 of the working electrode 2 with an insulating layer is preferable in order to regulate the area of the working electrode. However, such insulating layer can be omitted. When omitted, the area from the portion corresponding to the lead 4 to the working electrode 2 should function as an electrochemical working electrode. In this structure, it is preferable to form the working electrode 2 and the lead 4 with the same material.

The electrochemical analysis element in accordance with the present invention may comprise a three-electrode system further including a reference electrode in addition to the working 2 and counter 3 electrodes disposed on the inner wall of the hollow space 1 of the sensor body in order to stabilize measurement accuracy of the element.

The reagent segment 9 containing an enzyme may be positioned optionally if only it is located inside the hollow space; however, it is particularly preferred to dispose it on the working electrode 2.

Figure 3:
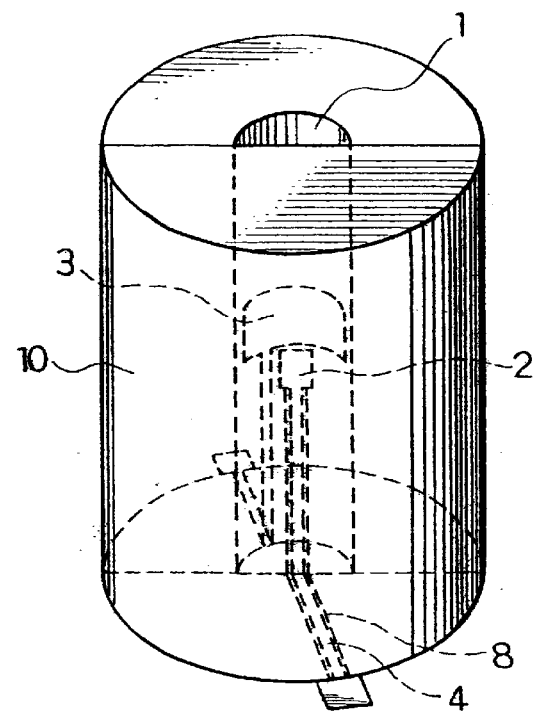
FIG. 3 is an oblique view illustrating an electrochemical analysis element in accordance with another example of the present invention from which the reagent segment has been omitted.
Figure 4:
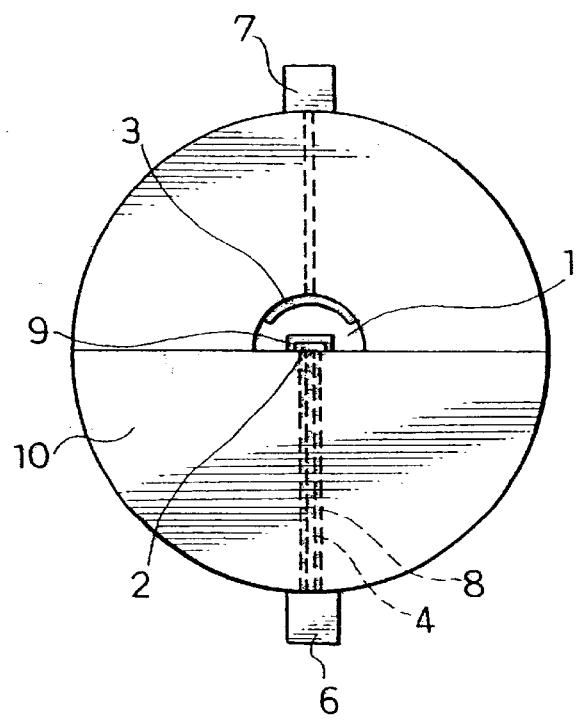
FIG. 4 is a plan view of the same element.
Figure 5:
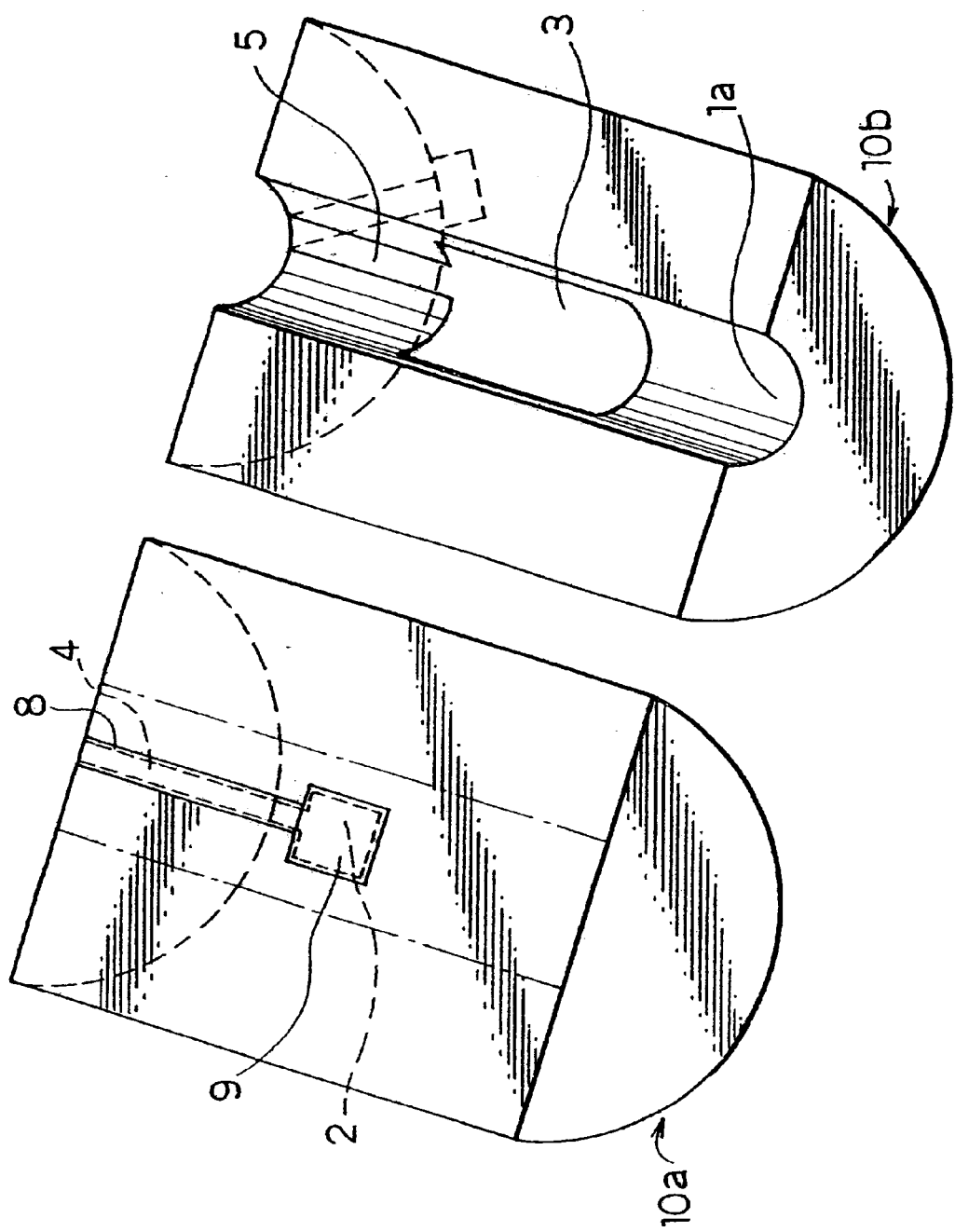
FIG. 5 is an exploded oblique view of the element of FIG. 3.

The hollow space 1 of the sensor body 10 may have an arbitrary shape and is not necessarily limited to cylindrical shape. FIG. 3 and FIG. 4, respectively, show other examples of the electrochemical analysis element in accordance with the present invention. In FIG. 3, the reagent segment 9 has been omitted. FIG. 5 is an exploded view of the element of FIG. 3 into a first part and a second part. The sensor body 10 is composed of a first part 10a and a second part 10b. The hollow space 1 is formed by closing a semi-circular groove 1a formed in the second part 10b with the first part 10a. The working electrode 2 and the lead 4 connected thereto are formed on a plane opposed to the groove 1a of the first part 10a. An insulating layer 8 for coating the lead 4 is also formed on the same plane. For more accurate control of the area allowed for the working electrode to exhibit its action, the working electrode 2 can be coated with the insulating layer around its periphery. In the groove 1a of the second part 10b, the counter electrode 3 and the lead 5 connected thereto are formed. The counter electrode 3 may be disposed on the first part 10a.

The above-mentioned electrode system and leads can be disposed on the inner wall of the hollow space of the sensor body using a known method such as sputtering or the like. They may be formed by sputtering with the necessary portions being masked. Otherwise, unnecessary portions may be removed by means of laser trimming or the like after the whole area is sputtered. As an alternative, the electrode system and the leads may be formed by adhering an appropriate metal foil onto the sensor body by heating or ultrasonically melting the sensor body. In forming the leads and the electrodes, any known conductive material may be used. Examples of the material are carbon, silver, platinum, gold and palladium.

The reagent segment may be arranged in the hollow space of the sensor body in the following fashion.

An aqueous solution containing an enzyme is dropped on the inner wall of the hollow space of the sensor body using a pipette or something like that and dried. Alternatively, the reagent segment may be formed by immersing the sensor in an aqueous solution containing an enzyme, followed by drying. Latter method enables uniform distribution of the reagent segment on the inner wall of the hollow space.

The electrochemical analysis element in accordance with the present invention also permits formation of the reagent segment by dropping an aqueous solution containing a hydrophilic polymer in addition to an enzyme on the inner wall of the hollow space of the sensor body, followed by drying. The hydrophilic polymer enhances adhesion of the reaction layer onto the inner wall of the hollow space. Examples of such hydrophilic polymer may be carboxymethyl cellulose, hydroxyethyl cellulose, hydroxypropyl cellulose, methyl cellulose, ethyl cellulose, ethylhydroxyethyl cellulose, carboxymethylethyl cellulose, polyvinyl pyrrolidone, polyvinyl alcohol, polyamino acids such as polylysine, polystyrene sulfonate, gelatin and its derivatives, polyacrylic acid and its salt, polymethacrylic acid and its salt, starch and its derivatives, or a polymer of maleic anhydride or its salt.

The electrochemical analysis element in accordance with the present invention also permits further inclusion of an electron acceptor in the reagent segment if occasion demands. The electron acceptor may be exemplified as ferricyanide ion, p-benzoquinone and its derivatives, phenazine methosulfate, methylene blue, or ferrocene and its derivatives. One or more of those electron acceptors are used.

Figure 6:
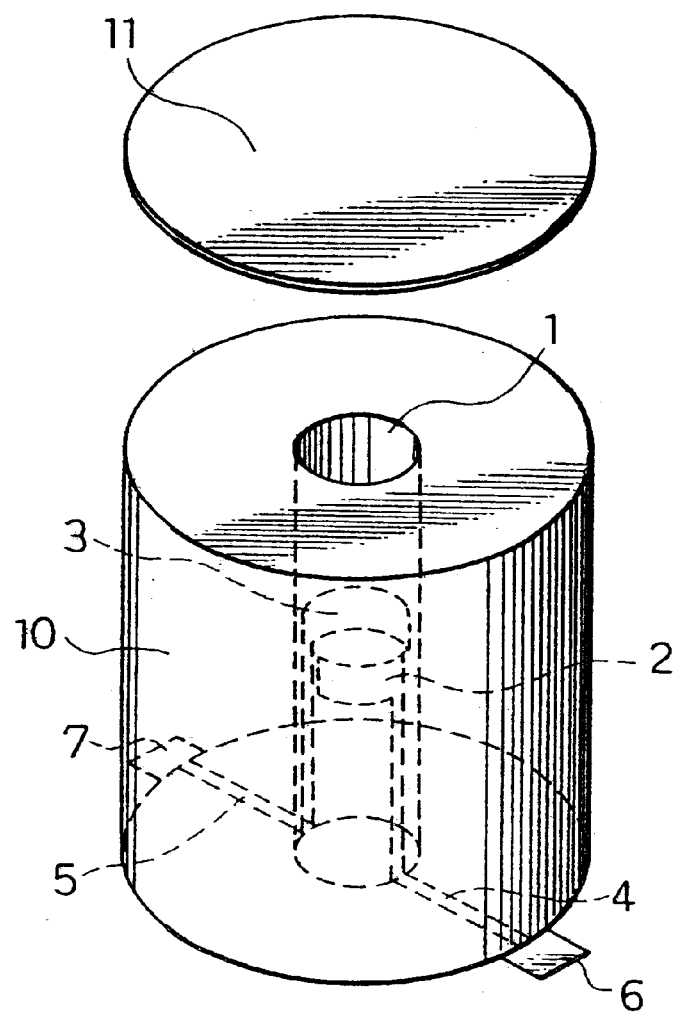
FIG. 6 is an oblique view illustrating an electrochemical analysis element in accordance with a further example of the present invention from which the reagent segment has been omitted.

As shown in FIG. 6, it is preferable for the electrochemical analysis element in accordance with the present invention to have a filter 11 adhered to the upper open end of the hollow space 1 which open end will be used as a sample supply port. The filter 11 filters red blood cells when whole blood sample passes therethrough.

Figure 7:
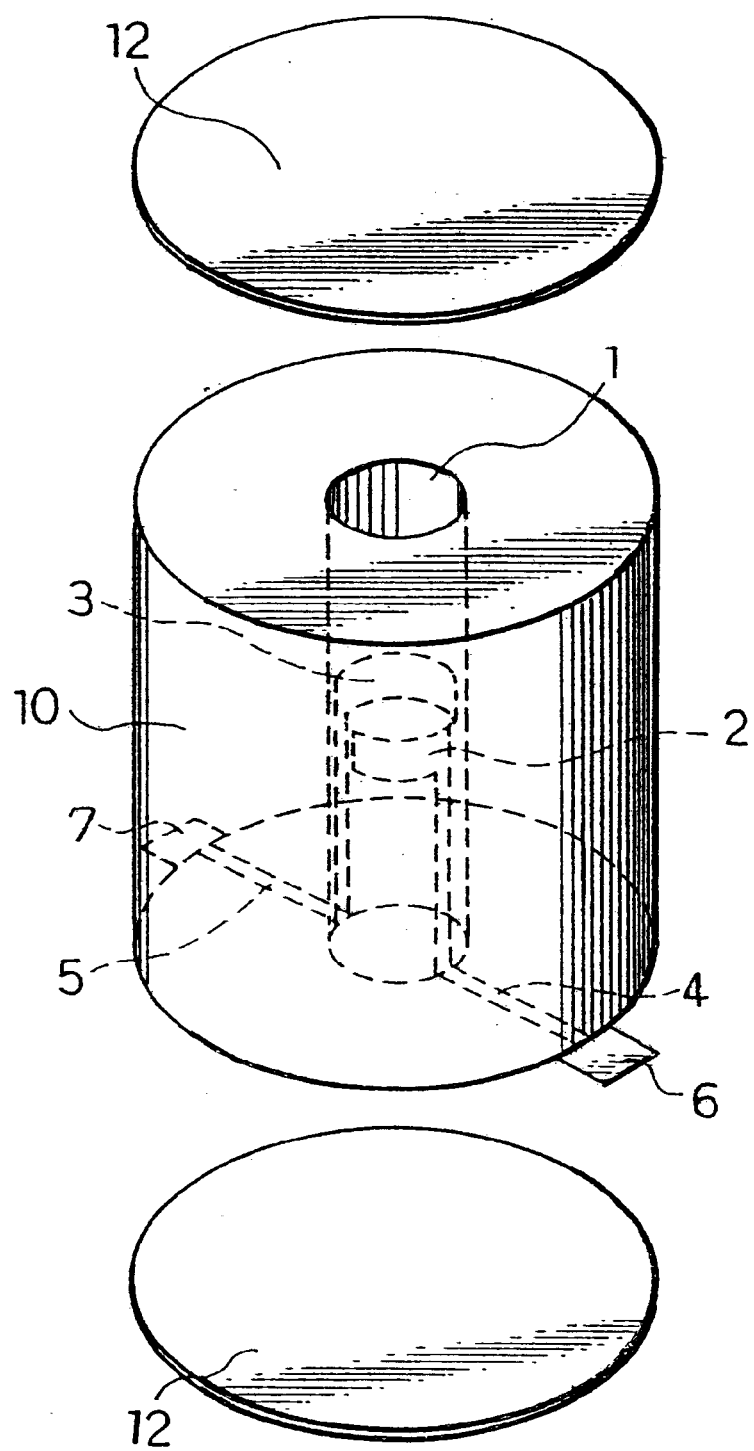
FIG. 7 is an oblique view illustrating an electrochemical analysis element in accordance with a still further example of the present invention from which the reagent segment has been omitted.

As shown in FIG. 7, the electrochemical analysis element in accordance with the present invention also allows to cover both open ends of the hollow space 1 with a film 12 made of a sealing material. Although this structure requires removal of the film 12 at use of the element, provision of the film yields an improving effect on the reliable preservation of the reagents contained in the reagent segment.

In the following, operations of the electrochemical analysis element in accordance with the present invention will be described.

First, a sample solution containing a specific component (substrate) is supplied in the hollow space 1 of the sensor body from one open end of the hollow space. Upon supply of the sample, the reagent segment containing an enzyme dissolves in the sample solution and the substrate contained in the sample solution selectively reacts with the enzyme in the reagent segment. As a result, oxidation of the substrate by the enzyme proceeds and oxygen present in the sample solution is reduced to hydrogen peroxide. Subsequently an appropriate voltage is applied onto the electrode system and the hydrogen peroxide formed is oxidized. Response current flowing across the electrode system during this oxidation reaction is proportional to the concentration of hydrogen peroxide produced, that is, substrate concentration in the sample solution. Therefore, the substrate concentration in the sample can be determined by simply measuring such response current value.

Preliminary impregnation of the reagent segment with some appropriate electron acceptor should produce a reduced form electron acceptor upon enzyme reaction, in place of production of hydrogen peroxide. Subsequently, an appropriate voltage is applied onto the electrode system and the reduced form electron acceptor is oxidized. Response current flowing across the electrode system during this oxidation reaction is proportional to the concentration of the reduced form electron acceptor produced, that is, substrate concentration in the sample solution. Therefore, the substrate concentration in the sample solution can be determined by simply measuring such response current.

If the electrode system is arranged on a plane and the amount of available sample solution is very small, resistance against inter-electrode charge transfer, mainly ion transfer increases. This may sometimes produce variations in the measurement results. As shown above, the electrochemical analysis element in accordance with the present invention enables an opposed arrangement of the working electrode to the counter electrode on the inner wall of the hollow space of the sensor body. This arrangement can smooth inter-electrode ion transfer, thereby increasing the accuracy of measurement. Smaller sizes of the hollow space of the sensor body facilitate supply of a sample solution onto the electrode system by capillary phenomenon, by simple placement of the sample on one open end of the hollow space. Therefore, the electrochemical analysis element of the present invention enables measurement of even a trace amount of sample with high accuracy.

As noted above, the electrochemical analysis element of the present invention quantitates a specific component in a sample by supplying the sample onto the electrode system disposed in the hollow space of the, sensor body. A method for sampling blood or the like from the body may be to press one open end of the hollow space of the sensor body against the skin surface of the host to damage the skin by actuating the body fluid leaking instrument from the other open end of the hollow space. The blood bleeding from the damaged site is then conveyed to the hollow space directly from the open end in contact with the skin. The body fluid leaking instrument may be laser beam emitting device, lancet or something like that.

Figure 8:
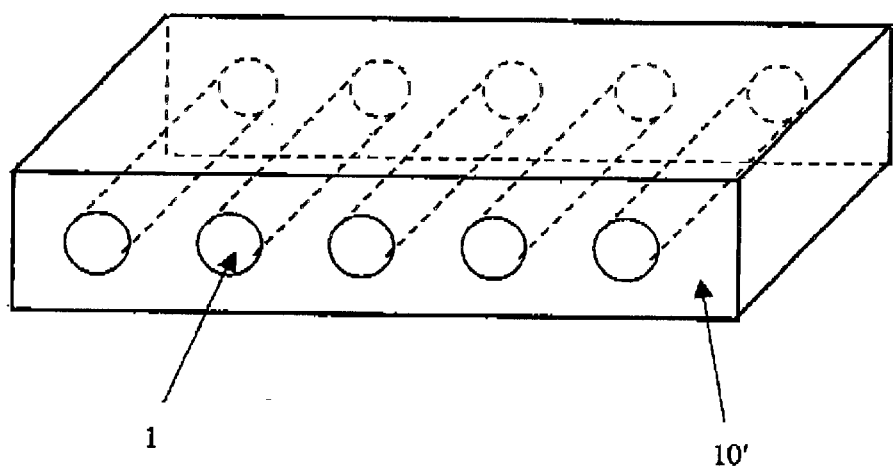
FIG. 8 is an oblique view illustrating an electrochemical analysis element in accordance with yet another example of the present invention in which the sensor body is band-like with a plurality of holes arranged along the length of the sensor body.
Figure 9:
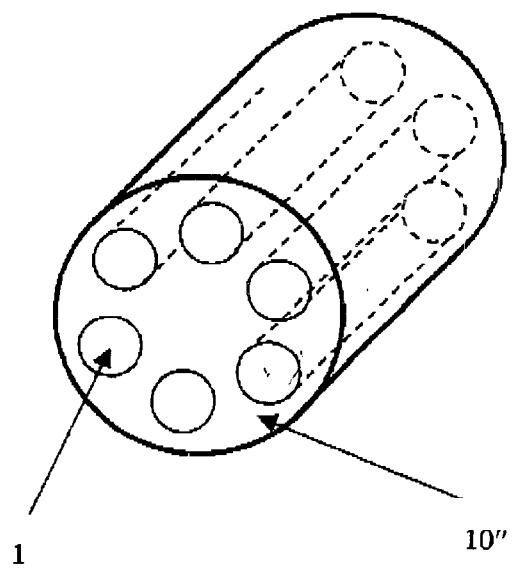
FIG. 9 is an oblique view illustrating an electrochemical analysis element in accordance with an alternative arrangement of the plural holes of FIG. 8 arranged instead in a circle along a periphery of a disc.

In the below-described examples, the sensor body is cylindrical and the sensor body accommodates only one sensor. However, the electrochemical analysis element in accordance with the present invention is not limited to the above shape and number of sensor For example, as shown in FIG. 8, the sensor body 10' may be a hand-like extended insulating member having plural holes 1 penetrating up and down which are arranged along the length of the sensor body to form the electrode system (not shown) in each hole, that is, hollow space. This structure can produce a sensor body which includes a plurality of analysis elements. Otherwise, as shown in FIG. 9 the sensor body 10" may be an insulating disc member having plural similar holes 1 penetrating up and down which are arranged like a circle along the periphery of the disc. This structure also produces a sensor body having a plurality of analysis elements. As such, when plural elements are combined, it is preferable to design an optimal arrangement of the electrode leads (not shown) of the respective elements and their connections to the forming measurement device to allow free selection of a specific element.

In the following, the present invention will be described by means of specific examples of electrochemical analysis element. However, the present invention is not limited to those examples. In the figures used in explaining each example, common elements were designated by the same numerals and, if appropriate, explanation has been omitted partially.

EXAMPLE 1

A working electrode 2, a counter electrode 3, a lead 4 and another lead 5 each made of a platinum material were formed on the inner wall of a hollow space 1 of a sensor body 10 by means of sputtering. On the lead 4, an insulating layer was adhered by heat-melting an insulating polymer thin film. An aqueous solution of glucose oxidase (hereinafter abbreviated to "GOD") was dropped on the working electrode 2 and dried to form a reagent segment 9. In this way, an electrochemical analysis element of Example 1 was produced.

The element was evaluated for its response characteristics in the following manner.

An aqueous glucose solution as a sample solution was supplied from an upper open end of the hollow space 1, that is, from the side opposite to the side disposed with lead connectors 6,7. Thirty seconds after supply of the sample solution, a voltage (+0.7 V) was applied onto the working electrode 2, taking the counter electrode 3 as standard. The current flowing 5 seconds after voltage application was measured. The current value measured here was proportional to the concentration of hydrogen peroxide produced upon enzyme reaction, that is, glucose concentration in the sample solution.

EXAMPLE 2

The working electrode 2, counter electrode 3, leads 4, 5 and insulating layer for coating the leads 4,5 were formed in the same manner as in Example 1 except for the use of carbon material in place of platinum material and the use of printing method in place of sputtering method. On the working electrode 2, an aqueous solution containing GOD as an enzyme and potassium ferricyanide as an electron acceptor was dropped and dried to form the reagent segment 9. As shown in FIG. 6, a filter 11 mainly composed of glass fiber was also provided to make contact with an upper open end of the hollow space. This gave an electrochemical analysis element of Example 2.

An aqueous glucose solution was supplied to the element in the same manner as in Example 1 but via the filter 11 and response characteristics of the element was evaluated. The result showed that the glucose concentration was proportional to the response current as measured. Next, whole blood was supplied to the element as a sample via the filter 11 and the response characteristics of the element was evaluated. The filter 11 filtered red blood cells during passage of the supplied whole blood therethrough and only plasma reached the reagent segment 9. The reagent segment 9 dissolved in the plasma and glucose in the plasma was oxidized by GOD. At that time, ferricyanide ions in the reagent segment were reduced to form ferrocyanide ions. Thirty seconds after supply of the whole blood, a voltage (+0.5 V) was applied onto the working electrode 2 to oxidize ferrocyanide ions, taking the counter electrode 3 as standard. The current flowing 5 seconds after voltage application was measured. The current value measured here was proportional to the concentration of ferrocyanide ions produced by oxidation of ferricyanide ions, that is, concentration of glucose in the blood.

EXAMPLE 3

A similar electrochemical analysis element was produced in the same manner as in Example 2, except for the use of cholesterol oxidase in combination with cholesterol esterase in place of GOD. This element was used to attempt quantitative analysis of the total concentration of cholesterol ester and free cholesterol (hereinafter abbreviated to "total cholesterol") in whole blood. Blood cholesterol ester produced free cholesterol by the catalyst reaction of cholesterol esterase. The free cholesterol thus produced was oxidized together with such free cholesterol that is originally present in the whole blood. At that time, ferricyanide ions in the reagent segment were reduced to form ferrocyanide ions. Three minutes after supply of whole blood, a voltage (+0.5 V) was applied onto the working electrode 2 to oxidize ferrocyanide ions, taking the counter electrode 3 as standard. The current flowing 5 seconds after voltage application was measured. The current value measured here was proportional to the concentration of ferrocyanide ions produced by oxidation of ferricyanide ions, that is, total cholesterol concentration in the blood.

As discussed above, the present invention can provide an electrochemical analysis element which facilitates very accurate and rapid quantitation of a substrate (specific component) in a trace amount of biological sample such as blood, urine, etc. or food sample such as food raw material or food product from food industries.

Although the present invention has been described in terms of the presently preferred embodiments, it is to be understood that such disclosure is not to be interpreted as limiting. Various alterations and modifications will no doubt become apparent to those skilled in the art to which the present invention pertains, after having read the above disclosure. Accordingly, it is intended that the appended claims be interpreted as covering all alterations and modifications as fall within the true spirit and scope of the invention.

What is claimed is:

1. A method for analyzing a biological sample, comprising (a) providing an electrochemical analysis element comprising a sensor body having a hollow space which space is open at both of its ends, both ends being arranged along an axis of the element, an electrode system including a working electrode and a counter electrode and a reagent segment containing an enzyme, wherein said electrode system and said reagent segment are disposed on an inner wall of said hollow space, (b) pressing one of the open ends of the hollow space against a skin portion of a host from whom a sample is to be analyzed, and (c) introducing the sample into the hollow space through a filter disposed on the one open end.

2. The method according to claim 1, wherein the working electrode is positioned opposite to the counter electrode on the inner wall of the hollow space.

3. The method according to claim 1, wherein the reagent segment further comprises an electron acceptor.

4. The method according to claim 1, wherein the reagent segment is disposed on the working electrode.

5. The method according to claim 1, wherein the sample is introduced into the hollow space by capillary action.

6. The method according to claim 1, wherein the hollow space has a capillary size to facilitate supply of the sample by capillary transport from one end of the space to the electrodes.

7. The method according to claim 1, further comprising (d) providing a body fluid leaking instrument and (e) actuating the body fluid leaking instrument to damage the skin portion of the host to release the sample to be analyzed.

8. The method according to claim 7, wherein the body fluid leaking instrument is selected from the group consisting of a laser beam emitting device and a lancet.

9. The method according to claim 7, wherein the hollow space has a size that allows for passage of the body fluid leaking instrument from the one open end to the other open end.

10. The method according to claim 1, wherein the sample to be analyzed comprises whole blood and the filter filters out red blood cells.

11. A method for analyzing a biological sample according to claim 1, wherein each open end is covered with a film.

12. The method according to claim 11, wherein the film comprises a sealing material.

13. The method according to claim 12, wherein the film is selected from the group consisting of resin and aluminum laminate.

14. A method for analyzing biological samples according to claim 1, wherein the sensor body has a plurality of said hollow spaces, and step (b) comprises selectively pressing one of the open ends of each hollow space against a skin portion of a host from whom samples are to be analyzed, such that samples are directly and selectively introduced into different ones of the hollow spaces.

15. The method according to claim 14, wherein the sensor body is an insulating disc member and the hollow spaces are arranged along the periphery of the disc member.

16. The method according to claim 14, wherein the analysis element has a cylindrical shape.

17. The method according to claim 14, wherein each hollow space has a circular or semicircular cross sectional shape.

18. The method according to claim 14, wherein the analysis element has a substantially uniform length.

* * * * *